United States Patent [19]
Kurtz

[11] 3,940,478
[45] Feb. 24, 1976

[54] PROTEOLYTIC ENZYMES AS ADJUNCTS TO ANTIBIOTIC PROPHYLAXIS OF CONTAMINATED WOUNDS

[75] Inventor: Leonard D. Kurtz, Woodmere, N.Y.
[73] Assignee: Sutures, Inc., Coventry, Conn.
[22] Filed: Apr. 29, 1974
[21] Appl. No.: 465,309

[52] U.S. Cl. ................................................. 424/94
[51] Int. Cl.² .......................................... A61K 37/48
[58] Field of Search ..................................... 424/94

[56] References Cited
UNITED STATES PATENTS
2,973,300   2/1961   Farrar et al. ........................... 424/94

FOREIGN PATENTS OR APPLICATIONS
2,036   9/1963   France .................................. 424/94

Primary Examiner—Stanley J. Friedman
Attorney, Agent, or Firm—Larson, Taylor and Hinds

[57] ABSTRACT

In the delayed antibiotic treatment of contaminated open wounds by the administration of an antibiotic, the improvement comprising applying to the surface of the said wound, as an adjunct to said antibiotic treatment, a proteolytic enzyme in amounts sufficient to potentiate the activity of said antibiotic.

5 Claims, No Drawings

PROTEOLYTIC ENZYMES AS ADJUNCTS TO ANTIBIOTIC PROPHYLAXIS OF CONTAMINATED WOUNDS

FIELD OF THE INVENTION

This invention relates to an improvement in the antibiotic prophylaxis of contaminated wounds. More particularly, the invention is directed to a method of potentiating the activity of antibiotics employed therapeutically in the treatment of contaminated open wounds to prevent the subsequent development of infection therein.

BACKGROUND OF THE INVENTION

Antibiotics have long been used prophylactically in the treatment of contaminated wounds whether inflicted surgically or through injury. The success of the antibiotics in these treatments is directly related to the time in which the antibiotic is administered. If the contaminated wound is treated with the antibiotic immediately the development of infection is prevented. Should there be a delay in the antibiotic treatment, however, the therapeutic value of the antibiotic is minimized, especially in the case of contaminated open wounds where the failure of delayed antibiotic treatment to prevent infection is particularly evident. It has been found, for instance, that contaminated open wounds subjected to closure as little as three hours after injury become infected despite treatment with antibiotics at the time of closure. It is highly likely then that a large number of wounds are destined to develop infection despite antibiotic therapy since traumatic injuries incurred in either military conflicts or civilian accidents are subjected to an inevitable delay in treatment, the most rapid and modern rescue transit systems, notwithstanding.

That there exists, therefore, a real need for a method that improves or enhances the therapeutic value of antibiotics in these cases where treatment of contaminated open wounds is delayed is readily apparent. Satisfaction of this need is the main object of the invention. Other objects will become apparent to those of ordinary skill in the art as the description of the invention proceeds.

SUMMARY OF THE INVENTION

According to the invention it has been found that in the antibiotic treatment of contaminated open wounds to prevent or at least reduce the subsequent development of infection therein the therapeutic activity of the antibiotic is potentiated by applying onto the surface of the wound, as an adjunct to the antibiotic treatment, a proteolytic enzyme.

DETAILED DESCRIPTION OF THE INVENTION

The mechanism and precise manner by which the proteolytic enzyme potentiates the effectiveness of the antibiotics is not completely understood. It is believed, however, that the mechanism that accounts for the success of the enzymes as adjuncts to the antibiotic treatment is that the enzymes facilitate contact of the antibiotic with the bacteria. The reason for the failure of antibiotics to prevent infection in the delayed treatment of contaminated wounds is attributed to the film of proteinaceous coagulum the body tends to form on the surface of open wounds. This coagulum in the course of its development apparently surrounds the bacteria and prevents the antibiotic from gaining access to the pathogen. The proteolytic enzyme works on the coagulum to disrupt or otherwise break it down thereby permitting access of the antibiotic to the otherwise entrapped or shielded bacteria.

By the term "adjunct" as used herein and in the appended claims is meant use of the proteolytic enzymes jointly with the antibiotic treatment and includes use either prior to, simultaneous with or after administration of the antibiotic. Application of the proteolytic enzyme before or simultaneously with the antibiotic treatment is preferred but application of the proteolytic enzyme immediately after systemic administration of the antibiotic is feasible. Best results are achieved, however, by application of the proteolytic enzyme prior to the antibiotic treatment.

Application of the proteolytic enzymes can be effected, for instance, by using a suitable solution of the enzyme, preferably a saline solution, and applying the enzyme solution to the wound in a conventional manner. The use of ointments of the enzymes or similar carrier mediums which tend to limit the enzymes contact with the wound or are otherwise deleterious to the wound and impair its ability to resist infection should be avoided. Certain ointments containing the proteolytic enzyme, for instance, have failed to alter the infection rate of the contaminated wounds. The time in which the enzyme is in contact with the wound prior to the application of the antibiotic has been correlated with its effectiveness as an adjunct to delayed antibiotic treatment. By the term "delayed antibiotic treatment" as used herein is meant that period of time after infliction of the wound after which antibiotic treatment alone will not prevent the development of infection. While minimum contact of the proteolytic enzyme with the wound before administration of the antibiotic, as where the antibiotic is administered immediately after application of the enzyme, provides substantial reduction in the rate of subsequently developed infection, greater effectiveness is achieved when a contact period of several minutes, for example, at least about 10 minutes, for the enzyme is allowed. Also, though single treatments with the proteolytic enzyme will potentiate the effects of delayed antibiotic activity it is preferred to use multiple applications of the proteolytic enzyme. The effectiveness of the proteolytic enzymes as an adjunct to delayed antibiotic treatment is enhanced by multiple treatments of the wounds with the enzymes.

In accordance with a preferred embodiment of the invention, after the enzyme has contacted the wound for a desired period of time, the wound is blotted with a dry gauze sponge. Blotting of proteolytic enzyme wounds treated in this manner have been found to remove bacteria from the wounds in far greater numbers than when the wounds are treated with saline. Cleansing of the proteolytic enzyme-treated wound by blotting with gauze sponge, however, removes only a small percentage of the total number of bacteria in the wound. The level of bacteria remaining after the blotting still remains well above the mean dose of bacteria necessary to produce infection and therefore although contributing to the potentiation of the effectiveness of the antibiotic its role is minor compared to the potentiation occuring through the enzymatic hydrolysis of the wound coagulum which enhances accessibility of the antibiotic to the bacteria.

The dosage of proteolytic enzyme will vary depending primarily upon the particular enzyme and antibiotic employed. In all cases, however, an effective amount sufficient to potentiate the activity of the antibiotic is utilized. Generally this concentration falls in the range of at least about 2,000 N.F. units per wound up to 50,000 or more N.S. units per wound, preferably about 20,000 to 30,000 N.F. units per wound.

Proteolytic enzymes, also commonly referred to as proteinases or proteases, by definition are enzyme compounds which hydrolyze, digest, depolymerize or otherwise degrade or decompose protein. Illustrative of proteolytic enzymes suitable for use in the invention are tripsin, pepsin, rennin, chymotrypsin, pankrin, enterokinase, chymopapain, ficin, bromelin, B. subtilis proteinase, insulinase, aspergillus proteinase, carboxypeptidase, protaminase, asparaginase, cerevase and rapidase. If desired, mixtures of proteolytic enzymes can be used.

The antibiotics employed in the present invention may be any of those commonly employed in the therapeutic treatment of contaminated open wounds of animals including man. Administration of the antibiotics can be either topically or systemically. The route by which the antibiotic is administered does not preclude use of the proteolytic enzymes. As examples of suitable antibiotics for use in the invention there can be included the "pencillins" such as Penicillin G, N, O and V, nafcillin, methicillin, oxacillin benzylpenicillin and the like; cephalosporins such as cephalolexin, cephaloglycin, cephaloridine and cephalothin; polymyxins such as Polymyxin B, tyrothricin, vancomycin, neomycin, erythromycin, streptomycin, aureomycin, tetracycline, terramycin, gentamycin, novobiocin bacitracin and the like. The antibiotic dosages employed are those generally employed in the therapeutic treatment of contaminated wounds and will vary depending principally upon the particular antibiotic employed.

A note of caution should be made regarding application of the present invention. Where treatment with the proteolytic enzymes and antibiotics is delayed for too long a period, the combined therapy has no significant benefit. The actual delay period when this combined therapy fails to produce any significant benefit will vary among enzymes. In the case of the enzyme trypsin, for example, this delay period is about eight hours. In contaminated wounds subjected to an eight hour delay in treatment, application of tripsin and antibiotic onto the wound did not significantly alter the infection rate. For other enzymes this critical delay period may be longer or shorter. In any case, however, the period is readily determinable by routine investigation.

The invention will be further described by the following examples which are merely illustrative and should not be construed as limiting the invention in any way. In the examples the inflammatory responses assessed were wound induration and the presence of purulent exudate. Induration about the wound was determined by palpating the wound with the gloved finger on the fourth postoperative day. The indurated margin of each wound was measured in millimeters. After each measurement, the wound was opened and inspected for evidence of purulent exudate. In all groups of animals an estimate of the number of viable bacteria in the wound was made. After swabbing the length of each wound three times with a cotton tipped applicator, the applicator was immersed in a glass tube containing 5 ml of 0.9% sodium chloride. The tube was placed on a Vortex mixer for one minute. The number of bacteria suspended in saline was quantitated by standard microbiologic dilution techniques. The results are reported as the average logarithm of the bacterial count as this more accurately reflects the logarithmic growth of the organism. All results were subjected to statistical analysis utilizing a 95 percent confidence coefficient as a criterion of significance.

The proteolytic enzyme employed in the examples was trypsin. Trypsin is a pancreatic enzyme which preferentially catalyzes the hydrolysis of peptide bonds but also has some esterase and amidase activity. The crystalline trypsin employed was a bovine origin and was assayed by the National Formulary method using N-benzoyl-L-arginine ethyl ester hydrochloride as the substrate. The enzyme was dissolved in 0.9% saline before each experiment and then immediately added to the designated wounds.

EXAMPLE I

Five groups of guinea pigs were prepared for study in the following manner: Two standardized incisions, parallel and equidistant from the vertebral column were made in each guinea pig. Five minites after surgery each wound was contaminated with 0.02 ml. of 0.9% sodium chloride containing $10^6$ organisms of a penicillin sensitive strain of Staphylococcus aureus. Previous experiments have indicated that this inoculum is the minimal infective dose that will elicit infection in untreated wounds. After bacterial contamination the wounds remained open and untreated for three hours.

In four groups of animals, the contaminated wounds were subjected to a topical application of 0.1 ml of solution containing different concentrations of the proteolytic enzyme trypsin. The doses of enzyme were 2,500, 10,000, 25,000, and 50,000 N.S. units/wound. The wounds in the remaining group served as the controls and received a topical application of 0.1 ml of 0.9% sodium chloride. The solutions remained on the wounds for twenty minutes before being blotted with a sterile gauze sponge. Five minutes after blotting, the wounds were subjected to topical benzylpenicillin ($100,000\mu$) applied topically in 0.1 ml of sodium chloride onto the surface of each wound. Five minutes after completing treatment in these groups as well as in other groups, the edges of the wound were closed by tape. The inflammatory responses of all wounds were measured on the 4th post-operative day.

The results of the study were reported in table I.

Table I

| Animal* (no.) | Treatment | Induration (mm) | (p) | Gross Infection (% positive) | (p) | Viable Bacteria (log) | (p) |
|---|---|---|---|---|---|---|---|
| 9 | 0.9% sodium chloride | 6.9 ± 1.2 | — | 100.0 | — | 5.40 ± 0.38 | — |
| 4 | 2,500 units Trypsin | 4.3 ± 0.7 | <0.01 | 44.0 | 0.01 | 3.144 ± 2.20 | 0.015 |
| 5 | 10,000 units Trypsin | 4.3 ± 0.7 | <0.01 | 40.0 | 0.01 | 3.260 ± 2.10 | 0.015 |
| 4 | 25,000 units Trypsin | 4.4 ± 0.7 | <0.01 | 0.0 | <0.002 | 0.657 ± 0.94 | 0.003 |

Table I-continued

| Animal* (no.) | Treatment | Inflammatory Responses | | | | | |
|---|---|---|---|---|---|---|---|
| | | Induration (mm) | (p) | Gross Infection (% positive) | (p) | Viable Bacteria (log) | (p) |
| 5 | 50,000 units Trypsin | 4.5 ± 0.8 | <0.05 | 0.0 | <0.002 | 2.192 ± 0.57 | 0.003 |

*Each wound received a standard inoculum of $7.2 \times 10^6$ S. aureus.

The data of Table I show that the effectiveness of proteolytic enzymes as adjuncts to topical antibiotics can be correlated with the dose of the proteolytic enzymes. Contaminated wounds subjected to 2,500 N.F. units of trypsin topically prior to delayed antibiotic treatment had a lower infection rate (44%) than the control wounds subjected to only the antibiotic (100% infection) ($p<0.01$). A similar level of gross infection (40%) was encountered when 10,000 N.F. units of trypsin was applied to the contaminated wound before antibiotic treatment. The benefits of proteolytic enzymes were most apparent in contaminated wounds receiving concentrated solutions of enzymes prior to delayed antibiotic treatment. A combination of either 25,000 N.F. units of trypsin/wound or 50,000 N.F. units trypsin/wound prevented the development of wound infection.

The gross infection scores for the wounds in this study could be correlated with the width of the indurated edges of the wounds and the viable bacteria recovered from the wound. The width of indurated edges of the wounds subjected to only the topical antibiotic were larger than the width of the indurated margins of wounds subjected to the proteolytic enzyme and the antibiotics. Similarly, the number of viable bacteria recovered from the surface of wounds subjected to only the antibiotic were significantly greater than the number of viable bacteria in wounds receiving the enzyme as an adjunct to the antibiotic. These differences between the viable bacterial count of wounds subjected to only the antibiotic and those receiving combined therapy was most apparent in wounds treated with 25,000 N.F. units of trypsin prior to the topical antibiotic. In these wounds, the bacterial count was approximately 10,000 fold lower than the bacterial count of wounds subjected to only the antibiotic.

EXAMPLE II

The purpose of this example was to correlate the period of time in which the enzyme was in contact with the wound with the success of delayed antibiotic treatment. The guinea pigs were prepared and infected as described in Example I above and then divided into five treatment groups. Three groups of wounds received topical applications of 0.1 ml of 25,000 N.F. units of trypsin. In designated groups of animals the proteolytic enzyme remained on the wounds for 10, 20 and 30 minutes before being blotted. Following this treatment, these wounds were subjected to the topical antibiotic. In another group of guinea pigs 25,000 N.F. units of trypsin and 10,000 units of benzylpenicillin were added simultaneously to each wound without blotting before wound closure. The wounds in the fifth group served as controls and received a 30 minute treatment with 0.1 ml of 0.9% sodium chloride before being blotted and treated with the antibiotic.

The results of the study are reported in Table II below.

Table II

| Animal* (no.) | Treatment** | Inflammatory Responses | | | | | |
|---|---|---|---|---|---|---|---|
| | | Induration (mm) | (p) | Gross Infection (% positive) | (p) | Viable Bacteria (log) | (p) |
| 5 | 0.9% sodium chloride 30 minutes | 6.6 ± 0.8 | — | 80.0 | — | 4.996 ± 0.54 | — |
| 6 | 0 minutes | 4.9 ± 1.0 | NS*** | 25.0 | 0.05 | 3.218 ± 1.20 | 0.006 |
| 5 | 10 minutes | 5.1 ± 0.3 | <0.05 | 0.0 | 0.002 | 2.657 ± 1.40 | 0.006 |
| 6 | 20 minutes | 5.2 ± 0.4 | <0.01 | 0.0 | 0.002 | 2.351 ± 1.30 | 0.004 |
| 7 | 30 minutes | 4.6 ± 1.1 | NS | 0.0 | 0.002 | 1.60 ± 1.30 | 0.004 |

*Each wound received a standard inoculum of $7.2 \times 10^6$ S. aureus.
**Treatment involved application of 25,000 N.F. units of trypsin for a specified period of time.
***Not Significant The data of Table II show that the effectiveness of proteolytic enzymes as potentiators of antibiotic activity in delayed antibiotic treatment is related to the time in which the enzyme is in contact with the wound prior to the application of the antibiotic. When the antibiotic was applied to the wound immediately after treatment with 25,000 N.F. units of trypsin, 25% of the wound developed subsequent infection as compared to the 80% gross infection score for contaminated control wounds treated with only the antibiotic. In wounds subjected to contact with the enzyme for 10 minutes prior to antibiotic treatment none of the wounds developed infection. Absence of infection was also encountered in wounds subjected to prolonged contact with the enzyme prior to treatment with the antibiotic.

The data also indicates that prolonged contact of the wound with the proteolytic enzyme prior to antibiotic treatment may facilitate wound sterilization for as the period of contact between the enzyme was extended, the number of viable bacteria recovered from the surface of the wound was decreased. The number of viable bacteria recovered from wounds subjected to the enzyme for 30 minutes prior to antibiotic treatment was significantly lower than the bacterial count of wounds subjected to the proteolytic enzyme for shorter periods.

EXAMPLE III

The purpose of this example was to identify the importance of repetition of application of the proteolytic enzyme, as opposed to a single treatment, as a determinant of the success of trypsin as an adjunct to topical antibiotics in contaminated wound treatment. In this study the animals were divided into eight treatment groups. In the wounds subjected to a proteolytic enzyme, 10,000 N.F. units of trypsin in 0.1 ml saline were applied to the wound for 10 minute time intervals. After each treatment, the wounds were blotted with a dry gauze sponge. In four groups of animals the wounds received either one, two, three or four successive applications. Four other groups of guinea pigs served as controls. The contaminated wounds in these control animals were subjected to a comparable number of applications of 0.1 ml of 0.9% sodium chloride. Five minutes after completing the last treatment in each group of animals, a topical antibiotic was applied to each wound as in Example I prior to wound closure.

The results are summarized in Table III below.

EXAMPLE IV

The purpose of this experiment was to examine the therapeutic value of the proteolytic enzyme as an adjunct to delayed treatment with antibiotic administered by a systemic route. Guinea pigs were prepared and contaminated as in Example I. In one group of animals, each wound was subjected to a topical application of 25,000 N.F. units of trypsin. After the enzyme remained on the wound for ten minutes, the wound was blotted with a sterile gauze sponge. The wounds in the second group of animals were subjected to 0.1 ml of 0.9% sodium chloride for 10 minutes followed by blot- Table III

| Animal* (no.) | Number of Applications | Treatment | Inflammatory Responses | | | | | |
|---|---|---|---|---|---|---|---|---|
| | | | Induration (mm) | (p) | Gross Infection (% positive) | (p) | Viable Bacteria (log) | (p) |
| 5 | 1 | 0.9% sodium chloride | 7.2 ± 1.0 | — | 81.2 | — | 6.142 ± 0.85 | — |
| 5 | 1 | 10,000 units Trypsin | 5.8 ± 0.4 | NS** | 40.0 | NS | 4.967 ± 1.47 | NS |
| 7 | 2 | 0.9% sodium chloride | 7.7 ± 1.1 | — | 100.0 | — | 6.099 ± 0.56 | — |
| 7 | 2 | 10,000 units Trypsin | 5.1 ± 0.9 | <0.01 | 21.4 | <0.01 | 4.191 ± 1.57 | 0.015 |
| 7 | 3 | 0.9% sodium chloride | 6.6 ± 0.6 | — | 78.6 | — | 6.123 ± 0.61 | — |
| 6 | 3 | 10,000 units Trypsin | 5.6 ± 1.0 | 0.05 | 0.0 | <0.01 | 4.129 ± 1.20 | 0.002 |
| 5 | 4 | 0.9% sodium chloride | 7.1 ± 0.9 | — | 70.0 | — | 6.205 ± 0.26 | — |
| 6 | 4 | 10,000 units Trypsin | 5.4 ± 0.9 | NS | 0.0 | <0.01 | 3.526 ± 2.00 | 0.006 |

*Each wound received a standard inoculum of $6 \times 10^6$ S. aureus.
**Not Significant The results of the tests show that while a single treatment with trypsin is effective in reducing the rate of infection in delayed antibiotic treatment of contaminated wounds, multiple treatments of the wounds with the enzyme definitely enhance its effectiveness. Wounds subjected to three or four successive applications of the enzyme before delayed antibiotic treatment had no infection.

With regard to wound sterilization, multiple applications of the proteolytic enzyme may not be as effective as a single application of the enzyme containing an equivalent dosage. The mean bacterial count of the wounds subjected to three or four successive applications of 10,000 N.F. units of the proteolytic enzyme appeared to be higher than the mean bacterial count of wounds subjected to a single application of either 25,000 N.F. units or 50,000 N.F. units of trypsin. This apparent ineffectiveness of successive applications of the enzyme as compared to a single treatment with an equivalent dose may be a reflection of the experimental design. The experiments involving multiple applications of enzymes were performed at a different time from those studies concerned with a single application of varying doses of the proteolytic enzymes. Small differences in the level of the bacterial inoculum utilized in these wounds may account for the variations in the number of bacteria recovered from the wound.

ting with a gauze sponge. Five minutes after blotting each animal received an intraperitoneal injection of benzylpenicillin (200,000 units).

The results are reported in Table IV.

Table IV

| Animal* (no.) | Treatment | Inflammatory Responses | | | | | |
|---|---|---|---|---|---|---|---|
| | | Induration (mm) | (p) | Gross Infection (% positive) | (p) | Viable Bacteria (log) | (p) |
| 6 | 0.9% sodium chloride | 6.0 ± 0.4 | — | 100.0 | — | 5.533 ± 0.32 | — |
| 8 | 25,000 units Trypsin | 4.9 ± 0.6 | NS** | 19.0 | 0.002 | 4.08 ± 0.64 | <0.001 |

*Each wound received a standard inoculum of $5.6 \times 10^7$ S. aureus.
**Not Significant The data of Table IV show that proteolytic enzymes potentiate the therapeutic value of systemic antibiotics. The gross infection score for wounds treated with trypsin in animals subjected to delayed treatment with a systemic antibiotic was 19%. This infection rate was significantly lower than the incidence of infection (100%) in control wounds subjected to only 0.9% saline at the time of administration of the systemic antibiotic. The number of viable bacteria recovered from the surface of wounds was proportional to the incidence of wound infection. The number of viable bacteria recovered from wounds treated with the proteolytic enzymes was significantly lower than that noted in the control wounds subjected to only 0.9% sodium chloride.

A comparison between the number of viable bacteria recovered from wounds treated with 25,000 N.F. units of trypsin and a topical antibiotic and the bacteria in wounds subjected to the same dose of the proteolytic enzyme and a systemic antibiotic suggests that topical antibiotics may enhance wound sterilization. The number of viable bacteria in wounds treated with the proteolytic enzyme and a topical antibiotic was lower than the number of bacteria in wounds subjected to the proteolytic enzyme and a systemic antibiotic. The statistical significance of this comparison can not be realized since the inoculum delivered to the wounds in the treatment groups were different.

EXAMPLE V

The purpose of this portion of the study was to assess the therapeutic benefit proteolytic enzymes alone, without the aid of the antibiotic imparts to the contaminated wound. After preparation and contamination of the animals as described in Example I, the wounds in a group of guinea pigs were left open and untreated for three hours. After this time, the animals were separated into three treatment groups. Wounds in two groups of animals were treated with three successive applications of trypsin (10,000 N.F. units). Each application of trypsin remained on the wound for ten minutes before being blotted with sterile gauze. The wounds in the remaining group were subjected to three successive 10 minute applications of 0.9% sodium chloride. After each treatment with saline, the wounds were blotted. In one group of animals in which the wounds were subjected to topical proteolytic enzymes, the wound edges were approximated immediately with tape. For the remaining animals in which the wounds were subjected to the enzyme, 10,000 u of topical benzylpenicillin were applied to the wound prior to wound closure. This treatment group was included in this study to determine if any therapeutic benefits derived from treatment of the wound with proteolytic enzymes could be potentiated by the addition of an antibiotic to the regimen. Topical antibiotic treatment was also initiated in the group of guinea pigs whose wounds were subjected to only 0.9% sodium chloride.

The results are reported in Table V.

taminated wound. The incidence of infection in wounds treated with the proteolytic enzyme alone (50%) was significantly lower than the infection rate of the wounds treated with only the topical antibiotic (100%). The viable bacteria recovered from the surface of wounds subjected to delayed treatment with the proteolytic enzyme was lower than the surface bacterial counts of wounds treated with the antibiotic, but these differences were not statistically significant. A combination of topical proteolytic enzymes and antibiotics prevented the development of infection. The surface bacterial counts of wounds subjected to this combined therapy was significantly lower than the surface bacterial counts recovered from wounds in the other treatment groups.

It is claimed:

1. A method for the prophylactic treatment of contaminated but non-infected, open wounds to prevent or at least reduce subsequent development of infection therein which comprises applying to the film of proteinaceous coagulum formed on the surface of said contaminated but non-infected open wounds a proteolytic enzyme in an amount of at least 2,000 N.F. units per wound to break down said film of proteinaceous coagulum.

2. The improvement of claim 1 wherein the proteolytic enzyme is trypsin.

3. The improvement of claim 1 wherein the amount of proteolytic enzyme is about 2,500 to 50,000 N.F. units per wound.

4. The improvement of claim 3 wherein the amount of proteolytic enzyme is about 20,000 to 30,000 N.F. units per wound.

Table V

| Animal* (no.) | Treatment | Inflammatory Responses | | | | | |
|---|---|---|---|---|---|---|---|
| | | Induration (mm) | (p) | Gross Infection (% positive) | (p) | Viable Bacteria (log) | (p) |
| 5 | 0.9% saline × 3 + Penicillin | 6.6 ± 0.8 | — | 90.0 | — | 5.44 ± 0.70 | — |
| 7 | 10,000 u Trypsin × 3 | 6.4 ± 1.2 | NS** | 50.0 | 0.01 | 5.20 ± 0.97 | NS |
| 5 | 10,000 u Trypsin × 3 + Penicillin | 4.8 ± 0.8 | 0.01 | 0.0 | 0.002 | 4.64 ± 0.81 | <0.04 |

*Each wound received a standard inoculum of 1.2 × 10⁷ S. aureus.
**Not Significant The results of the tests show that proteolytic enzymes alone without the aid of the antibiotic have a significant therapeutic value in the delayed treatment of the con- 5. The improvement of claim 1 wherein multiple applications of said proteolytic enzyme are employed.

* * * * *